United States Patent [19]

Gutierrez et al.

[11] 4,420,621

[45] Dec. 13, 1983

[54] PREPARATION OF POLYCARBOXYLIC COMPOUNDS

[75] Inventors: Eddie N. Gutierrez, Fort Lee; Vincent Lamberti, Upper Saddle River, both of N.J.

[73] Assignee: Lever Brothers Company, New York, N.Y.

[21] Appl. No.: 217,347

[22] Filed: Dec. 17, 1980

Related U.S. Application Data

[60] Continuation of Ser. No. 47,859, Jun. 12, 1979, abandoned, which is a continuation of Ser. No. 905,308, May 12, 1978, abandoned, which is a division of Ser. No. 642,804, Dec. 22, 1975, Pat. No. 4,123,459.

[51] Int. Cl.$^3$ .................... C07D 307/32; C07C 51/38
[52] U.S. Cl. .................................. 549/322; 562/595
[58] Field of Search ...................... 549/322; 562/595

*Primary Examiner*—Norma S. Milestone
*Attorney, Agent, or Firm*—James J. Farrell

[57] ABSTRACT

Novel methods for preparing polycarboxylic compounds which are useful as metal sequestrants and food acidulants are disclosed. These compounds are aconitic acid and a mixture of aconitic acid, and the lactones of isocitric acid and alloisocitric acid. The compounds can be neutralized to the corresponding salts which, in turn, are metal sequestering agents. The novel methods include chlorination of propane-1,1,2,3-tetracarboxylic tetraesters.

5 Claims, No Drawings

PREPARATION OF POLYCARBOXYLIC COMPOUNDS

This is a continuation application of Ser. No. 47,859 filed June 12, 1979 now abandoned which was a continuation application of Ser. No. 905,308 filed May 12, 1978 now abandoned which was a divisional application of Ser. No. 642,804 filed Dec. 22, 1975 now U.S. Pat. No. 4,123,459.

This invention broadly relates to novel processes for the preparation of aconitic acid and a mixture of aconitic acid and the lactones of isocitric acid and alloisocitric acid. These compounds, while useful in themselves as metal sequestering agents, may be neutralized to form the alkali metal salts corresponding to the particular compound employed. These salts are, in turn, metal sequestering agents and/or detergent builders. The acid forms are useful as food acidulants. The lactone compounds may be easily converted into the corresponding hydroxy acid forms which also have utility as food acidulants.

The prior art methods of preparing aconitic acid were practically limited to natural fermentation and dehydration of citric acid (see U.S. Pat. No. 2,566,172; and Hentschel, J. Prakt Chem. (2) 35, 205 (1887). Although a synthetic method for aconitic acid has been proposed in the article by Michael, J. Prakt Chem. (2) 49, 21 (1894), this method has not been commercialized. Similarly synthetic methods for preparation of the lactones of isocitric acid and alloisocitric acid have been proposed by Pacher and Vickery, J. Biol. Chem. 163 169–184 (1946) and Gawron et al, J.A.C.S. 80 5856–5860 (1958) but do not appear to have been commercialized.

Accordingly, an object of the present invention is to provide a synthetic process for producing aconitic acid and a mixture of aconitic acid and lactones of isocitric acid and alloisocitric acid.

A further object is to produce the above compounds by a process which lends itself to commercial application.

Other objects and advantages will appear as the description proceeds.

The attainment of the above objects is made possible by this invention which includes chlorination of a propane-1,1,2,3-tetracarboxylic compound having the formula (I)

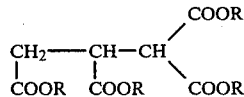  (I)

wherein R independently represents a lower primary alkyl of 1–4 carbon atoms such as methyl, ethyl, propyl, and butyl, to form a chlorinated tetracarboxylic compound. This compound is then saponified and dehydrochlorinated at a pH of about 9–11 preferably by heating with an alkali metal or alkaline earth metal hydroxide at temperatures of 25°–100° C. to form a propene tetracarboxylate derivative. Acidification of this derivative below a pH of about 8 produces aconitic acid and a mixture of aconitic acid and the lactones of isocitric acid and alloisocitric acid. The aconitic acid is initially obtained in both cis and trans forms. However, on work-up, which involves evaporation of the acidified solution to a residue, most of the cis aconitic acid is converted to trans aconitic acid. Similarly, in the mixture where both the aconitic acid and lactones appear, isocitric acid and alloisocitric acid are obtained initially in the reaction mixture. On work-up, which involves evaporation of the acidified solution, the isocitric acid and alloisocitric acid are mainly converted to the lactone forms.

The subject invention, encompassing novel synthetic processes for the preparation of aconitic acid, or a mixture of aconitic acid and the above-described lactones, overcomes one or more of the disadvantages of the prior art heretofore described. This is accomplished with the advantage that the compounds may be easily prepared in good yields.

The invention is hereinafter set forth in more detail, specific features thereof being particularly delineated in the appended claims.

In the practice of the present invention a tetraester of Formula I above is prepared. These tetraester compounds are known and can be prepared by a conventional Michael Reaction as set forth in Chapter 3, Volume 10 of the publication entitled "Organic Reactions", edited by Roger Adams et al and published in 1959 by John Wiley & Sons. These tetraesters of Formula I are treated in the following manner:

The tetraester is chlorinated at a pH of about 2 to about 8 and the resulting product (Formula II) is separated from the reaction mixture:

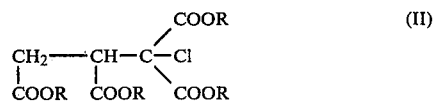  (II)

wherein R is as previously defined. In the general case, the chloro-tetraester is then dehydrohalogenated and saponified in an aqueous medium containing an alkali metal hydroxide or calcium hydroxide, strontium hydroxide or barium hydroxide to form a mixture of a 1,1,2,3-propene tetracarboxylate salt and a 1-hydroxy propane-1,1,2,3-tetracarboxylate salt. The mixture of salts is then acidified and decarboxylated to produce a mixture of aconitic acid and the above-described lactones.

In the general case under relatively stronger alkaline conditions, i.e. at a pH above about 9, the reaction of the above-described compound of Formula II proceeds as in the reaction diagram of Table I following:

TABLE I
---
REACTION DIAGRAM

TABLE I-continued
REACTION DIAGRAM

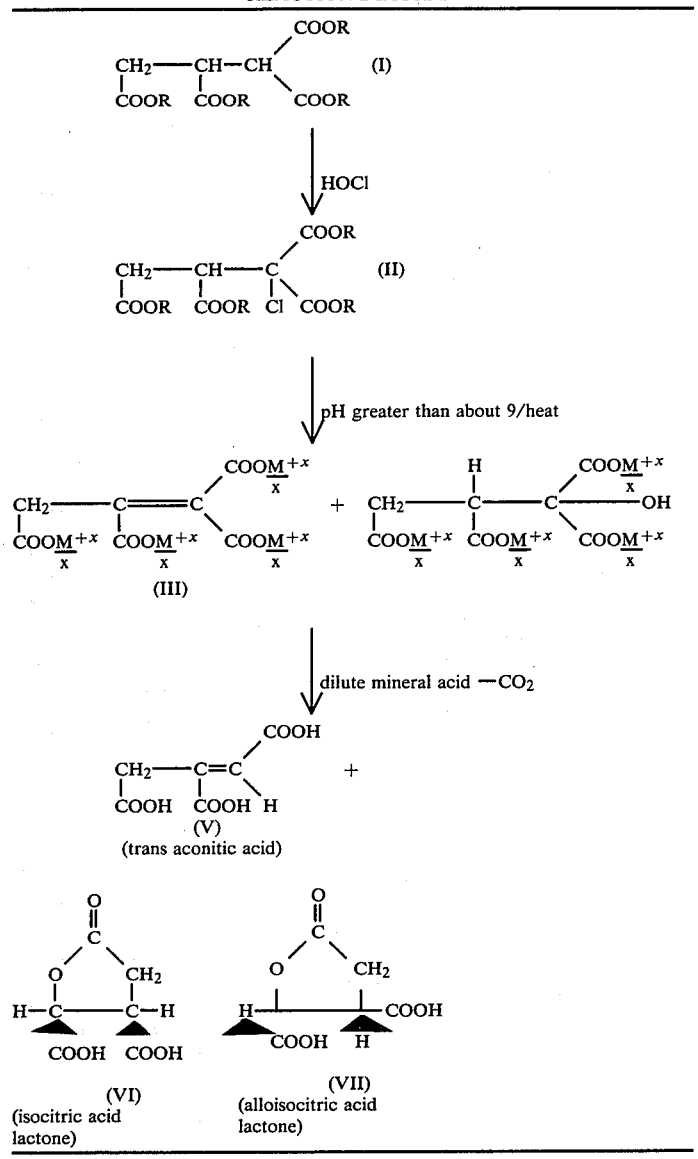

(VI)
(isocitric acid lactone)

(VII)
(alloisocitric acid lactone)

In the compounds, Formulas I through IV inclusive, R is as previously defined. M is a sodium, lithium, potassium, calcium, strontium or barium cation and x is 1 or 2 and is equivalent to the valency of M.

In the special case where magnesium hydroxide is used, a relatively weak alkaline reagent, i.e. a pH of about 9 or less, the final product of the same sequence of reactions is aconitic acid (Formula V) alone. The intermediate (Formula IV) is not formed and the intermediate Formula III, is formed, is only transient. In this special case M is Mg and x is 2 and R is as previously defined.

The compound of Formula I, as outlined in Table I, is chlorinated to form the compound of Formula II. The chlorination or reaction medium is preferably one in which the Formula I compound dissolves to facilitate a homogeneous reaction. However, the medium may be either water in which case the compound is dispersed or a cosolvent/water mixture in which the solvent preferably is miscible with water and serves to dissolve the Formula I compound.

Alternatively, the reaction may be carried out in the absence of water by utilizing an organic hypochlorite such as tertiary butyl hypochlorite. In this case the reaction preferably is carried out in the presence of an organic liquid which is compatible with the organic hypochlorite and the compound of Formula I. This organic liquid is suitably a lower alcohol such as methanol, butanol, isobutanol, t-butanol and halogenated hydrocarbons such as carbon tetrachloride.

When the reaction medium contains water, it must contain sufficient water to promote formation of the hypochlorous acid. This water maybe introduced as part of a hypochlorous acid solution to be added or may be already present in the reaction mixture which can then be treated with chlorine. Thus, the reaction medium may be all water or all cosolvent or any mixture of these. The total amount of reaction medium must be enough to effectively disperse or dissolve the reactants.

The ratio of the compound of Formula I to the total amount of reaction medium by weight is generally about 1:1 to 1:30 and preferably about 1:1 to 1:10. After introduction of the compound of Formula I into the reaction medium, a solution of a compound capable of generating HOCl is slowly added with stirring to the mixture to accomplish chlorination of the compound. The hypochlorous acid may be conveniently generated by an acidified solution of sodium hypochlorite. Generally, any alkali metal or alkaline earth metal hypochlorite under acidic conditions can be utilized but the sodium salts being readily available are preferred. The solution of sodium hypochlorite may be of any convenient concentration but dilute solutions of about 5% to about 15% by weight being readily available are preferred. The amount of HOCl required is about 1 to about 1.1 moles per mole of the compound of Formula I. If a substantially greater ratio of HOCl than 1.1 moles per mole of the compound of Formula I is utilized, it will not affect formation of the product but is uneconomical. If substantially less than one mole is employed, the reaction will not proceed to completion. When sodium hypochlorite is used, then a concurrent addition of a non-oxidizing mineral acid, such as for example, hydrochloric acid is employed to maintain a pH of less than about 8, preferably about 5 to about 7. If chlorine water is used, the pH is maintained below about 8, preferably about 5 to about 7 by the addition of alkali metal carbonates or hydroxides. The above pH range is used to maintain reasonable reaction rates.

The temperature of the above-described chlorination is usually about 0° to 50° C. to avoid premature decarboxylation prior to halogenation of the compound. Ambient temperatures are preferred as a matter of practicality and to keep side reactions to a minimum.

After the addition of the reactants, the reaction may be monitored by periodic sampling and NMR analysis since the characteristic NMR frequency of the methylene protons will shift from high field in the case of the compound of Formula I to a lower field as the chlorinated compound of Formula II is formed in the reaction medium. When the desired amount of chlorination is obtained, the chlorinated compound of Formula II may be isolated by conventional methods such as extraction. However, since the invention deals with a further reaction of this compound to produce aconitic acid (Formula V) or a mixture of aconitic acid (Formula V) and the lactones of isocitric acid (Formula VI) and alloisocitric acid (Formula VII), the reaction mixture containing the compound II is preferably retained and heated with the desired alkali metal or alkaline earth metal hydroxide to produce the aforesaid products.

Dehydrohalogenation and saponification is accomplished at a pH of about 9–12, more preferably about 9–10, and at temperatures of about 25° to 110° C. and preferably about 60° to 100° C. The reaction will still proceed although more slowly at the lower temperatures. To complete the reaction, the mixture is heated for about 3–4 hours with the concurrent addition of a selected alkali metal or alkaline earth metal hydroxides until saponification is complete. At this point the product is present as the alkaline earth metal or alkali metal salts of compound III or a mixture of the salts of compounds III and IV. In the special case where magnesium hydroxide is used, the pH is below about 9 and the product after dehydrohalogenation and saponification is magnesium aconitate. Conversion of magnesium aconitate or the salts of compounds III and/or IV into the final products, i.e. compounds V, VI and VII is accomplished by acidification with dilute mineral acid at a pH of preferably less than about 2. In the special case where the magnesium aconitate is acidified, aconitic acid is obtained.

In the cases wherein compounds III and/or IV are present, acidification involves a decarboxylation of the intermediate tetracarboxylic compound to produce a mixture of the compounds of Formulas V, VI and VII.

The following Examples will more fully illustrate the embodiments of this invention. All parts and proportions referred to herein and in the appended claims are by weight unless otherwise indicated.

EXAMPLE I

A. PREPARATION OF TETRAMETHYL PROPANE-1,1,2,3-TETRACARBOXYLATE

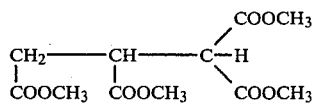

To 200 ml of methanol is added 0.1 gram of sodium metal. After the reaction is complete, 0.1 mole of dimethyl malonate is added. Next, 0.1 mole of dimethyl maleate is added and the resulting solution is refluxed for four hours. The reaction mixture is then distilled to yield the tetraester product: b.p., 146°–150° C. (2.0–3.0 mm Hg). The structure is confirmed by NMR analysis.

B. PREPARATION OF TETRAMETHYL PROPANE-1-CHLORO-1,1,2,3-TETRACARBOXYLATE

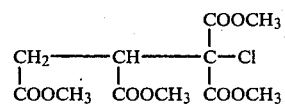

27 grams of the product prepared in I-A above is dissolved in 200 ml of 1:1 methanol:water by volume. 240 grams of sodium hypochlorite solution (5.2% by weight) is slowly added over a one-hour period while maintaining the pH at 3 to 7 by concurrent addition of dilute HCl (5%). The reaction mixture is evaporated to a syrup, which is then extracted with ether and the ether layer evaporated. The ethereal residue is distilled to give 26 grams (84% of theoretical yield) of product: b.p. 120°–130° C. (0.15 mm Hg) and m.p. 43.5°–49.3° C. The structure is confirmed by NMR analysis (in $CDCl_3$).

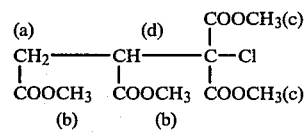

$CH_2$ (a) ABX multiplet, 2.80–3.00δ
$CH_3$(b) singlet, 3.70δ
$CH_3$(c) singlet, 3.84δ
CH(d) multiplet, 4.00–4.27δ

EXAMPLE II
PREPARATION OF ACONITIC ACID
Procedure A

Twenty six grams (0.085 mole) of product prepared as in Example I-B is mixed with 250 mls water. Thirty grams (0.5 mole) of magnesium hydroxide is slowly added during a 10 minute period. The reaction mixture is refluxed for 4-5 hours, cooled and acidified slowly with 101 grams of 25% sulfuric acid solution to a pH of 1.3. The mixture is then filtered, evaporated to dryness in vacuo and the residue extracted with acetone. The acetone solution is filtered and evaporated to dryness to give 22 grams of a residue containing 41% (62.6% yield) of trans-aconitic acid (determined by NMR analysis).

EXAMPLE III
PREPARATION OF A MIXTURE OF ACONITIC ACID AND THE LACTONES OF ISOCITRIC ACID AND ALLOISOCITRIC ACID
Procedure A Thirty one grams (0.1 mole) of product prepared as in Example I-B is mixed with 200 mls water. Thirty grams (0.4 mole) calcium hydroxide is added slowly while the pH of the reaction medium is maintained at 10-10.5 and the temperature is kept between 70° and 75° C. After the addition of calcium hydroxide is complete, the reaction mixture is stirred at 75° C. for an additional two hours and then cooled. 90 grams of a 20% by weight hydrochloric acid solution is added slowly to a pH of 1.3 and the resulting solution is then filtered. The filtrate is evaporated to dryness in vacuo and the residue extracted with acetone. The acetone extract is filtered and 19.5 grams of product consisting of 53.5% (60% yield) transaconitic acid and 5.8% of a mixture of lactones of isocitric acid and alloisocitric acid.

Procedure B

Thirty one grams (0.1 mole) of the product prepared in Example I-B is mixed with 300 mls water. 79 grams of strontium hydroxide (0.65 mole) is added slowly at 65°-70° C. while maintaining the pH at 10-10.5. The mixture is stirred for an additional three hours after the addition of the strontium hydroxide. The solution is cooled and 180 grams of 10% hydrochloric acid is added slowly to a pH of 1.3. The acidified solution is next evaporated to dryness in vacuo. The residue is extracted with acetone and the acetone extract is filtered and evaporated to dryness. There is thus obtained 23 g of residue containing 45.7% (60.5% yield) trans-aconitic acid and 10.7% of a mixture of the lactones of isocitric acid and alloisocitric acid.

Procedure C

Thirty one grams (0.1 mole) of the product prepared in Example I-B is mixed with 300 mls water. Forty four grams (0.29 mole) barium oxide is added over a ½ hour period while maintaining the temperature of the reaction medium at 60°-70° C. and the pH at 10-11. The mixture is heated for an additional two hours after all the barium oxide has been added. The mixture is then cooled and 216 grams of a 10% solution of hydrochloric acid is added. The acidified solution is evaporated to dryness to give 22.2 grams of residue containing 59.2% (75.5 yield) trans-aconitic acid and 9.8% of a mixture of the lactones of isocitric acid and alloisocitric acid.

Procedure D

Thirty one grams (0.1 mole) of the product prepared as in Example I-B is mixed with 200 mls water. Twenty three grams (0.58 mole) sodium hydroxide in 200 mls water, is slowly added while maintaining the temperature of the reaction medium at 70°-75° C. and the pH at 10-10.5. The solution is heated for an additional three hours until an NMR sample shows that hydrolysis is complete. The solution is acidified slowly with 162 g of 10% hydrochloric acid to give a pH of 1.2. The acidified solution is evaporated to dryness in vacuo and the residue is extracted with acetone. The acetone solution is filtered and evaporated to dryness to give 18.3 grams of a residue consisting of 53.5% (56% yield) and 32.6% (35% yield) of a mixture of the lactones of isocitric acid and alloisocitric acid (determined by NMR analysis).

EXAMPLE IV
A. PREPARATION OF DIBUTYL MALONATE 116 grams dimethyl malonate is dissolved in 500 mls butanol containing one gram of sodium metal. The solution is refluxed for 8 hours. The methanol is then distilled off and the reaction mixture is neutralized with concentrated hydrochloric acid and filtered. The excess butanol is next distilled off in vacuo to give a residue of 145 grams dibutyl malonate (structure verified by NMR).

B. PREPARATION OF DIBUTYL MALEATE

Seventy grams (0.63 mole) maleic anhydride is dissolved in 300 mls n-butanol containing one gram p-toluene sulfonic acid. The solution is refluxed for 16 hours during which the water formed is removed with a Dean Stark trap. The excess butanol is then distilled in vacuo to give a residue of 200 g of dibutyl maleate (structure verified by NMR analysis).

C. PREPARATION OF TETRABUTYL PROPANE-1,1,2,3-TETRACARBOXYLATE

One half gram of sodium metal is dissolved in 200 mls n-butanol and to this solution is added 108 g (0.5 mol) of dibutyl malonate. After reacting for five minutes, 114 grams (0.5 mole) of dibutyl maleate is added and the reaction mixture is refluxed for 6 hours. The solution is neutralized with a few drops of conc. hydrochloric acid and then filtered. The excess n-butanol is distilled off in vacuo to give 213 grams of a tetrabutyl propane-1,1,2,3-tetracarboxylate. The structure is confirmed by NMR analysis (CDCl$_3$)

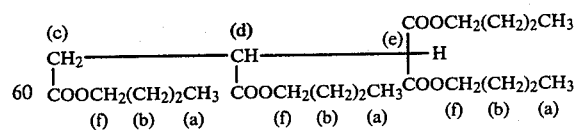

$CH_3$(a) multiplet at 0.84-1.12δ
$CH_2$(b) multiplet at 1.12-2.00δ
$CH_2$(c) multiplet at 2.67-2.90δ
CH(d) multiplet centered at 3.60δ
CH(e) doublet centered at 3.95δ
$CH_2$(f) 2 triplets, 4.00-4.30δ

D. PREPARATION OF TETRABUTYL 1-CHLOROPROPANE-1,1,2,3-TETRACARBOXYLATE

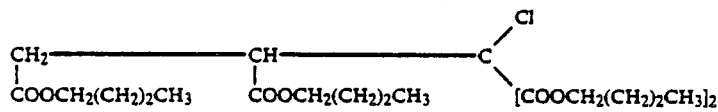

111 grams (0.28 mole) of the product prepared in Example IV-C is dissolved in a mixture of 200 mls methanol and 200 mls water. One liter of 5.25% NaOCl solution is slowly added with the concurrent addition of dilute hydrochloric acid to maintain the pH at 5–7. The resulting immiscible liquid is extracted with carbon tetrachloride and the CCl₄ extract is distilled in vacuo. A residue of 108 grams of tetrabutyl 1-chloropropane-1,1,2,3-tetracarboxylate is obtained. The structure is verified by NMR analysis (CDCl₃):

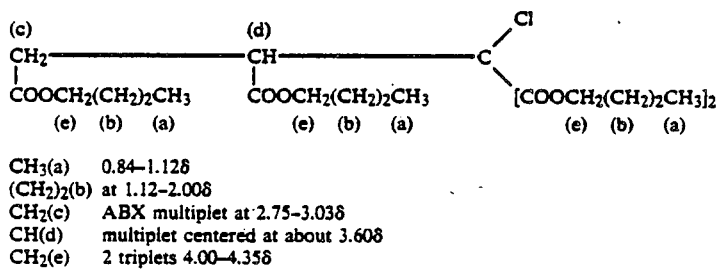

$CH_3(a)$   0.84–1.12δ
$(CH_2)_2(b)$ at 1.12–2.00δ
$CH_2(c)$   ABX multiplet at 2.75–3.03δ
$CH(d)$   multiplet centered at about 3.60δ
$CH_2(e)$   2 triplets 4.00–4.35δ

E. PREPARATION OF A MIXTURE OF ACONITIC ACID AND THE LACTONES OF ISOCITRIC ACID AND ALLOISOCITRIC ACID 25 grams (0.05 mole) of product obtained in IV-D is mixed with 100 mls water. Twenty one grams NaOH in 100 mls H₂O is added slowly while maintaining the pH at 10–11 and the temperature at 80°–85° C. 200 mls methanol is added to dissolve the ester and the solution is heated for 3 hours. The solution is then acidified to a pH of 1.3 with dilute hydrochloric acid and evaporated to dryness. The residue is extracted with acetone and the acetone extract (after filtering) is evaporated to dryness. There is obtained nine grams of a residue consisting of 42.3% (44% yield) of trans aconitic acid and 41.3% (38% yield) of a mixture of the lactones of isocitric acid and alloisocitric acid.

This invention has been described with respect to certain preferred embodiments and various modifications. Variations in the light thereof will be suggested to persons skilled in the art and are to be included within the spirit and purview of this application and the scope of the appended claims.

What is claimed is:

1. A process for preparing a mixture of aconitic acid and lactones of isocitric acid and alloisocitric acid comprising chlorinating a compound of the formula

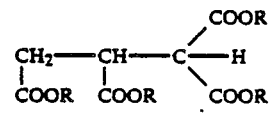

wherein R independently represents a lower primary alkyl group of 1 to 4 carbon atoms in an aqueous medium with hypochlorous acid to form a chlorinated tetraester; dehydrohalogenating and saponifying said chlorinated tetraester in an aqueous medium with $M/x+^xOH$, wherein M represents a lithium, sodium, potassium calcium, strontium or barium cation and x represents 1 or 2 and is equivalent to the valency of M, to form an aqueous mixture of propene and hydroxy propane compounds of the formulas

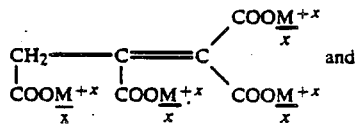 and

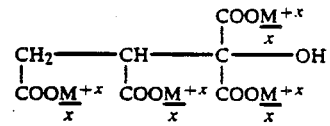

acidifying said aqueous mixture with a mineral acid to a pH of less than 2 to form said aconitic acid and said lactones.

2. A process as defined in claim 1 wherein said chlorination takes place at a pH of about 2 to about 8 and at a temperature of about 0° C. to about 50° C.

3. A process as defined in claim 1 wherein said dehydrohalogenation and saponification takes place at a pH of greater than 9 and at a temperature of about 25° C. to about 110° C.

4. A process as defined in claim 1 wherein said M is lithium, sodium or potassium.

5. A process as defined in claim 4 wherein said M is sodium.

* * * * *